United States Patent [19]

Ellis

[11] 4,292,968

[45] Oct. 6, 1981

[54] ELECTRIC SUPPLY FOR ION THERAPY

[75] Inventor: Franklin H. Ellis, Rochester, N.Y.

[73] Assignee: Sybron Corporation, Rochester, N.Y.

[21] Appl. No.: 97,535

[22] Filed: Nov. 26, 1979

[51] Int. Cl.³ .............................................. A61N 1/30
[52] U.S. Cl. ............................ 128/207.21; 128/419 R
[58] Field of Search .......... 128/207.21, 419 R, 420 R, 128/421, 422, 427, 419 F

[56] References Cited

U.S. PATENT DOCUMENTS

| | | | |
|---|---|---|---|
| 2,771,554 | 11/1956 | Gratzl | 128/421 |
| 3,489,152 | 1/1970 | Barbara | 128/422 |
| 3,521,641 | 7/1970 | Farensbach | 128/422 |
| 4,019,510 | 4/1977 | Ellis | 128/207.21 |
| 4,102,347 | 7/1978 | Yuki | 128/421 |
| 4,141,359 | 2/1979 | Jacobsen et al. | 128/207.21 |
| 4,175,565 | 11/1979 | Chierenza et al. | 128/419 F X |

OTHER PUBLICATIONS

Assimacopoulos, "Wound Heading . . . Current", The Am. Surgeon, Jun. 1968, vol. 34, No. 6, pp. 423-431.

*Primary Examiner*—Lee S. Cohen
*Attorney, Agent, or Firm*—Theodore B. Roessel; J. Stephen Yeo

[57] ABSTRACT

A power supply provides direct current to electrodes attached to a patient. The positive electrode is at least partially silver and releases silver ions as a result of the electric current. Silver ions have known bactericidal properties and may be used to treat infected living tissue. Tissue may, however, be damaged by voltages in excess of 1.1 volts. Accordingly, the power supply has two modes. Under normal conditions the power supply has a constant current output. If the voltage between the electrodes reaches a reference voltage of not more than 1.1 volt, the output is changed to a constant voltage mode, abruptly limiting the output voltage. A mode indicator may be incorporated in the supply.

1 Claim, 4 Drawing Figures

# 4,292,968

ELECTRIC SUPPLY FOR ION THERAPY

BACKGROUND OF THE INVENTION

This invention pertains to means for providing therapeutic silver ions and is more particularly concerned with a direct current source for releasing silver ions from an anodal electrode.

The bactericidal action of ionic silver has been known for years. It has been found that silver ions, when applied to tissue, will kill a broad spectrum of bacteria and other microorganisms. One source of silver ions is dissociable silver compounds which are topically applied to infected tissue.

A more effective ion source than silver compounds is a silver bearing electrode in close proximity to the tissue undergoing treatment. Usually the silver bearing electrode is positive in a direct current circuit. A return electrode, in contact with another area of the patient, provides a return path completing the circuit.

Direct current liberates ionic silver from the anodal electrode. The silver ions penetrate the infected tissue and bactericidal contaminants to a depth of about one centimeter. Because of the limited penetration the infected area is usually debrided prior to treatment.

Only small levels of direct current are needed. One worker, R. O. Becker, has found 300 MA satisfactory for treatment of chronic osteomyelitis. Current was supplied by a constant current generator.

The electrical resistance of both the tissue being treated and the tissue-electrode interface is a resistive load to the D.C. generator. In accordance with Ohm's law, inter-electrode voltage will increase with resistance if a constant current generator is used. At high resistance the voltage may exceed 1.1 volts whereupon half-cell electrolysis occurs and tissue is destroyed.

It is therefore an object of the invention to provide a direct current source for ionic therapy which provides a constant level of direct current under most normal load conditions while avoiding electrode voltages sufficient to cause electrolysis.

Another object is to provide a direct current source for ionic therapy having as two load-dependent modes constant current and constant voltage.

SUMMARY OF THE INVENTION

Briefly, the invention includes a electric power supply providing direct current through electrodes to tissue for the purpose of ionic therapy. The supply normally gives a constant current but limits the voltage between the electrodes to 1.1 volt or less to avoid damage to tissue. If the voltage is limited, the constant current may be divided between the electrode path and a shunt circuit. Indicating mean may be provided to indicate if the voltage is being limited and to indicate the current through the electrodes. In one embodiment one of the electrodes contains silver so silver ions are released into the tissue by the electric current.

DESCRIPTION OF THE INVENTION

According to the invention there is provided an electrical power source for supplying direct current through two electrodes in electrical contact with a patient. The anode electrode is at least partially silver as it has been found that silver evolving from an electrode will have a bactericidal action to adjacent tissue when the electrode is an anode in a low current circuit.

As a feature of the invention the power source has two modes of operation determined by the voltage between the two electrodes. This voltage is important because it has been found that when the inter-electrode voltage exceeds 1.1 volts, tissue damage occurs because of electrolysis.

Figure 1:
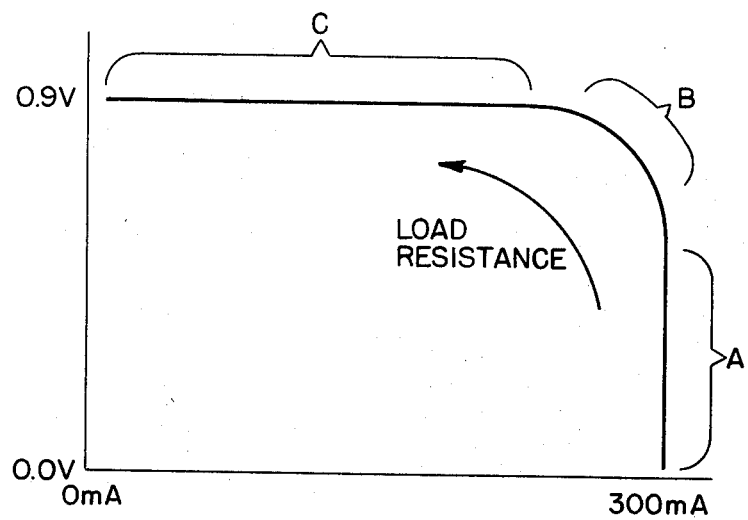
FIG. 1 is a curve representing the dual mode characteristics of a therapeutic power supply according to the invention.

Referring to FIG. 1, there is seen a curve representing the electrical output of the dual mode source, the independent variable being the electrical resistance between the patient electrodes.

At voltages below a predetermined limit below 1.1 volt the source will operate in a constant current mode. A current of about 300 microamperes has been successful in silver ion therapy. During the constant current mode the source provides a direct current at a constant amperage regardless of variations of load between the electrodes. Load variations may be due to resistance changes at the electrode-tissue interface such as a displaced electrode, an electrode which has become coated or polarized, or change in the electro-chemical characteristics of the tissue.

If the inter-electrode voltage should slightly exceed the predetermined voltage limit the supply shifts modes into constant voltage operation. This prevents the inter-electrode voltage from rising to levels when tissue damaging electrolysis may occur. To provide a safety factor a voltage less than 1.1 volts is chosen to be the determinating voltage limit. A maximum voltage of 0.9 volts was selected for the preferred embodiment for safety reasons.

The power supply's output is conditioned upon the voltage between the electrodes. At voltages below 0.9 volts the power supply will operate in the constant current mode, represented by the portion of the curve identified as "A". In this mode the output current will not be affected by changes in the resistance or load between electrodes. The voltage will, however, increase proportively with resistance. The current mode is maintained until the inter-electrode voltage reaches 0.9 volts whereupon there is a abrupt transition between constant current mode and constant voltage mode. The transition is the sharp knee, "B", of curve of FIG. 1. If the resistance increased even more, the voltage remains constant "C" while the current drops in accordance with Ohm's law. Because as the voltage is limited below 1.1 volt, electrolysis is prevented.

The mode transition between modes is much more abrupt than would occur with a diode voltage limiter which, being a square law device, does not provide a sharp transition.

Figure 2:
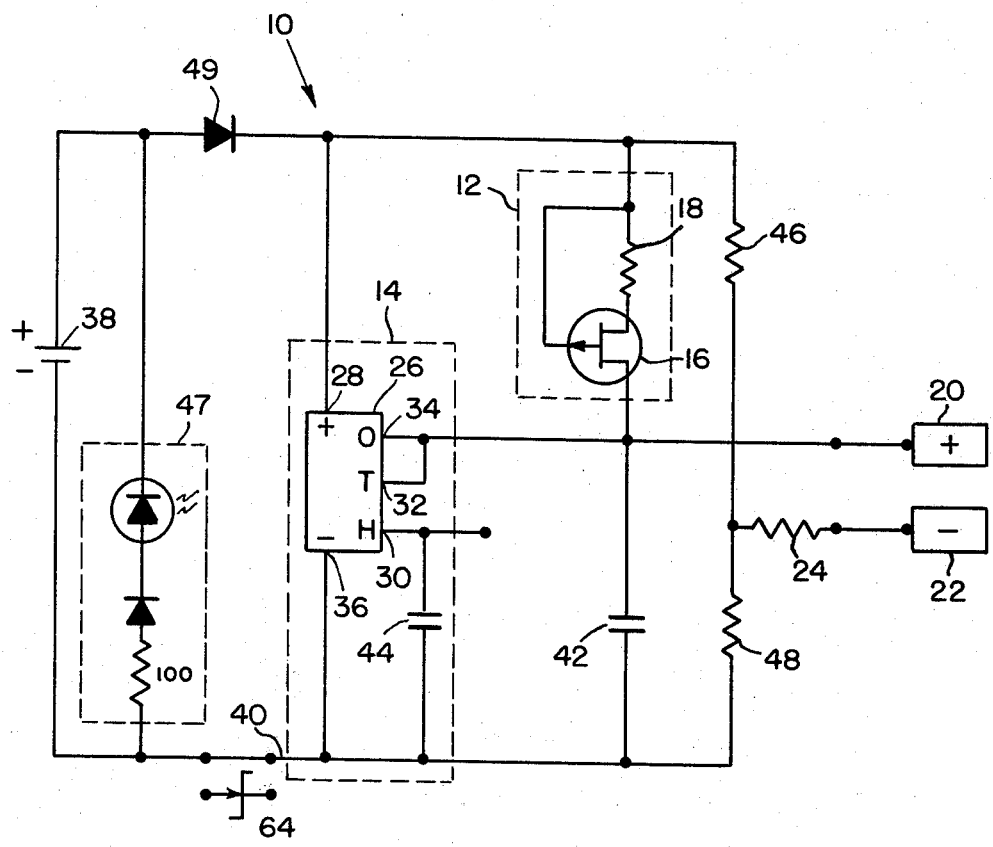
FIG. 2 is a schematic of the preferred circuitry of a power supply which embodies the invention.

The preferred embodiment of the invention is illustrated by the circuit schematic of FIG. 2. Typical component values are shown. The source 10 includes both a constant current generator 12 and a voltage limiter 14.

A suitable constant current generator is the well known arrangement of a field effect transistor 16 having its gate biased by the voltage across resistor 18. The generator current is determined by the value of resistor 18 and is independent of normal load variations. Resistor 18 may be a plurality of selectable resistors or a variable resistor so that different current levels may be obtained. The preferred current is, however, about 300 microamperes. During the constant current mode the entire current from the current source generator flows through the load via the electrodes 20, 22 and resistor 24.

Voltage limiter 14 is provided in shunt with the electrodes 20, 22 for limiting the output voltage across the electrode to below 1.1 volts.

The voltage limiter 14 functions as a variable resistive path shunting the electrodes 20, 22. When the inter-electrode voltage is less than 0.9 volts the limiter 14 presents a high resistance and all the current from the constant current generator flows through the electrodes 20, 22. If the inter-electrode voltage reaches 0.9 volts the resistance of the limiter 14 drops dividing the output of constant current generator between the electrode path and the limiter. The resistance of the limiter will decrease as necessary to limit the inter-electrode voltage to 0.9 volts.

In the circuit shown a commercially available integrated circuit 26 embodies the voltage limiter. The ICL8212 circuit manufactured by Intersil Inc., Cupertino Ca. was used. This circuit is a micropower bipolar monolithic intergrated circuit which includes an internal 1.15 volt voltage reference, a comparator and a pair of output buffer-drivers. Five pins connect to the integrated circuit. These pins are "positive power supply" 28, "hysterisis" 30, "threshold" 32, "output" 34, and "minus power supply" 36. A knowledge of the ICC8212 internal circuitry is not necessary to understand the invention.

As seen the positive power supply pin 28 is connected to the positive terminal of a battery 38 while the minus power pin 36 is connected to battery return 40.

The output of the current generator 12, the threshold pin 32 and the output pin 34 are electrically connected common to each other and the positive patient electrode 20. For silver ion therapy positive electrode 20 should be silver bearing. A capacitor 42 to battery return 40 prevents oscillation. The hysterisis pin 30 is capacitively coupled through capacitor 44 to battery return 40 to avoid noise. Two series resistors 46, 48 form a voltage divider which bias the negative patient electrode 0.25 volts above return 40. When the inter-electrode voltage is 0.9 volts, the voltage between the positive electrode 20 and return 40 is about equal to the internal reference voltage of 1.15 volts. Because this value is determined by the internal reference voltage and a fixed bias it shall be referred to in the claims as a reference voltage. This voltage level appears at the threshold pin 32 causing current to gradually be shunted to the output pin 34 from the electrodes 20, 22. As much current will be shunted as necessary to limit the interelectrode voltage to 0.9 volts.

In keeping with the invention is a LED indicator of battery reversal 47, and diode protection from battery reveral 49. The use of zener diode 64 will be explained in connection with FIG. 4.

As an additional feature of the invention, there may be provided means for indicating in which mode the source is functioning.

Figure 3:
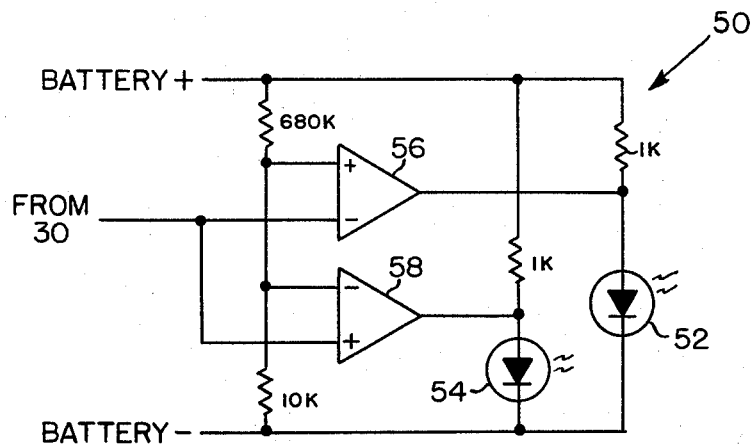
FIG. 3 is a schematic of a mode indicating circuit.

In FIG. 3 there is seen a binary display 50 having two LED's 52, 54 corresponding to the two modes.

The voltage at the hysterisis pin 30 is less than 0.1 volt during constant current mode and 0.4 volt during constant voltage mode. This voltage is directed to two voltage comparators 56, 58 which compares it to a reference voltage of about 0.1 volt provided by resistors.

Each comparator 56, 58 has a corresponding LED 52, 54 arranged at its output. The outputs are opposite and will change according to mode.

Figure 4:
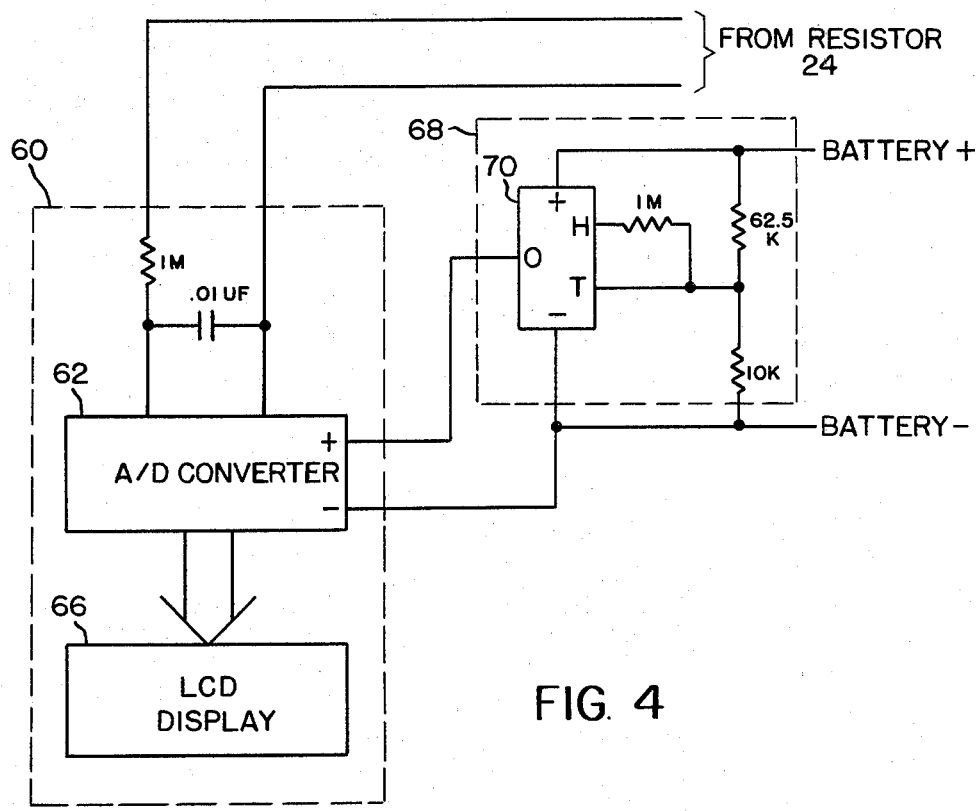
FIG. 4 is a schematic of a current indicating circuit for use with the circuit of FIG. 2.

An alternative indicating means is seen in FIG. 4. A digital volt meter 60 displays the treatment current passing between the electrodes 20, 22 as sensed by resistor 24 in series with the electrode path. The voltage across the resistor 24 corresponds the current and is directed to a A-D converter 62 such as an Intersil 5CL7106. A zener diode 64 may be needed to bias the input to a level acceptable to the A-D converter 62. The output of the converter 62 drives a liquid crystal display 66 which continuously indicates treatment current. A drop in current indicates such problems as a detached cable to the electrode, or a spent electrode.

The circuitry described is intended to be powered by a 9 volt battery. In keeping with the invention, a battery voltage indicator 68 may be provided. A ICL8212 circuit 70 normally enables the A-D converter 62. If the battery drops to approximately 7.5 volts, circuit 70 disables the A-D converter 62. The display 66 is blanked until battery voltage exceeds 8.0 volts.

The following parts list identifies some of the components used in actual circuits.

| | Semiconductors |
|---|---|
| FET 16 | 2N5461 |
| IC 26 | Intersil ICL8212CPA |
| Diode 49 | IN 914 |
| Comparator 56 | 1/2 LM 339 |
| Comparator 58 | 1/2 LM 339 |
| A/D Converter 62 | Intesil ICL 7106 |
| Zener 64 | IN5231B 5.1 volt |
| IC 70 | Intersil ICL8212CPA |
| | Resistors |
| 18 | 5.6 to 6.6k |
| 24 | 100 ohms |
| 46 | 3.9 to 4.9K |
| 48 | 150 ohms |
| | Capacitors |
| 42 | Sufficient to prevent oscillation |
| 44 | .68uf |

I claim:

1. Apparatus for ion therapy characterized by having two modes of operation and comprised of:
   two electrodes for making electrical contact with a patient;
   current means electrically connected to said electrodes for providing constant direct current flow through the electrodes during a first mode;
   voltage means electrically connected to said electrodes for providing a constant predetermined direct current voltage of less than 1.1 volts across the electrodes during a second mode; and
   voltage responsive means for causing an abrupt transition from the first mode to the second mode if the voltage across the electrodes reaches said predetermined voltage.

* * * * *